(12) United States Patent
Strassner et al.

(10) Patent No.: US 7,117,099 B2
(45) Date of Patent: Oct. 3, 2006

(54) WIDE BAND LAMBDA PROBE HAVING IMPROVED STARTING BEHAVIOUR

(75) Inventors: Walter Strassner, Schorndorf (DE); Lothar Diehl, Stuttgart (DE); Andreas Andorfer, Shanghai (CN)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/490,984

(22) PCT Filed: Aug. 13, 2002

(86) PCT No.: PCT/DE02/02959
§ 371 (c)(1),
(2), (4) Date: Oct. 13, 2004

(87) PCT Pub. No.: WO03/027462

PCT Pub. Date: Apr. 3, 2003

(65) Prior Publication Data

US 2005/0043899 A1 Feb. 24, 2005

(30) Foreign Application Priority Data

Sep. 26, 2001 (DE) ............................... 101 47 390

(51) Int. Cl.
*G01N 27/00* (2006.01)
(52) U.S. Cl. ............................ 702/24; 702/23; 702/31; 702/64; 204/424
(58) Field of Classification Search ............ 702/22–24, 702/64, 65, 30–32, 104, 189; 123/692–696, 123/672–674, 681, 688, 687; 204/424–427, 204/406; 73/23.2, 23.21, 23.32, 23.31, 31.05, 73/35.05–35.07
See application file for complete search history.

(56) References Cited

U.S. PATENT DOCUMENTS

| 4,172,432 | A | 10/1979 | Wessel et al. ............... 123/688 |
| 4,359,029 | A | 11/1982 | Furuhashi et al. .......... 123/681 |
| 5,675,069 | A | 10/1997 | Schleupen et al. ......... 73/23.32 |
| 6,073,083 | A | 6/2000 | Schnaibel et al. ............ 702/65 |
| 6,177,001 | B1 * | 1/2001 | Meyer ........................ 205/784 |
| 6,447,660 | B1 * | 9/2002 | Amtmann et al. .......... 204/425 |
| 6,767,442 | B1 * | 7/2004 | Scheer et al. ............... 204/425 |

FOREIGN PATENT DOCUMENTS

| DE | 25 59 046 | 7/1977 |
| DE | 197 28 926 | 1/1999 |
| DE | 199 41 051 | 3/2001 |

* cited by examiner

*Primary Examiner*—Hal Wachsman
(74) *Attorney, Agent, or Firm*—Kenyon & Kenyon LLP

(57) ABSTRACT

In a method and a control device for operating a broadband lambda sensor, the oxygen concentration of an exhaust gas is determined based on a comparison of a Nernst voltage with a reference voltage having a nominal value; a pump current is injected into a cavity of a pump cell if a deviation is present, an electric voltage present at the pump cell being regulated in such a manner that lambda=1 prevails in the cavity, the pump current being a measure for the value of lambda in the exhaust gas; and, in order to avoid control interference in the start phase of the engine or in the cold phase of the sensor, the Nernst voltage is maintained close to the reference voltage, using a pilot control, until the Nernst voltage is an actual measure for the oxygen concentration in the cavity of the pump cell.

9 Claims, 4 Drawing Sheets

WIDE BAND LAMBDA PROBE HAVING IMPROVED STARTING BEHAVIOUR

RELATED APPLICATIONS

This application claims priority of and is a U.S. national phase application of PCT/DE02/02959, filed Aug. 13, 2002, and claims priority to DE 101 47 390.7, filed in Germany on Sep. 26, 2001.

BACKGROUND INFORMATION

A lambda closed-loop control in conjunction with a catalytic converter is currently the most effective exhaust-gas treatment method for the spark-ignition engine. Only in interaction with currently available ignition and injection systems is it possible to achieve very low emission values. Especially effective is the use of a three-way catalytic converter, or selective catalytic converter. This type of catalytic converter is able to break down more than 98% of hydrocarbons, carbon monoxides and nitrogen oxides provided the engine is operated within a range of approximately 1% around the stoichiometric air-fuel ratio at lambda=1. In this context, lambda specifies the degree to which the actually present air-fuel mixture deviates from the value lambda=1, which corresponds to a mass ratio of 14.7 kg air to 1 kg of gasoline theoretically necessary for complete combustion, i.e., lambda is the quotient of the supplied air mass and the theoretical air requirement.

In lambda control, the given exhaust gas is measured and the supplied fuel quantity immediately corrected in accordance with the measuring result with the aid of the injection system, for instance. Used as sensor is a lambda sensor, which has a voltage jump at precisely lambda=1, in this way supplying a signal that indicates whether the mixture is richer or leaner than lambda=1. The effect of the lambda sensor is based on the principle of a galvanic oxygen-concentration cell with a solid state electrolyte.

Lambda sensors designed as two-step sensors operate in a manner known per se according to the Nernst principle, on the basis of a Nernst cell. The solid state electrolyte is made up of two boundary surfaces separated by a ceramic. The ceramic material that is utilized becomes conductive to oxygen ions at approximately 350 degrees Celsius, so that, given different oxygen concentrations on both sides of the ceramic, the so-called Nernst voltage is then generated between the boundary surfaces. This electric voltage is a measure for the difference in the oxygen concentrations on both sides of the ceramic. Since the amount of the residual oxygen in the exhaust gas of an internal combustion engine largely depends on the air-fuel ratio of the mixture conducted to the engine, the oxygen concentration in the exhaust gas may be utilized as a measure for the actually present air-fuel ratio.

In a rich mixture (Lambda<1), the sensor voltage supplied by the lambda sensor in accordance with the oxygen concentration in the exhaust gas reaches 800 to 1000 mV; in a lean mixture (Lambda>1), approximately 100 mV are still reached. The transition from rich to lean range occurs at around 450 to 500 mV. A stoichiometric ratio of air to fuel (Lambda=1) results in a sensor voltage of 450 mV. The mentioned values hold true for an operating temperature of the ceramic body of approximately 600 degrees Celsius, so that it must be heated accordingly during operation of the Lambda sensor.

The mentioned stepped voltage characteristic of the previously described lambda sensors allows a regulation in only a narrow value range around lambda=1. Therefore, these sensors are also called lambda=1 jump sensors. A substantial broadening of this measuring range, to lambda between 0.7 and 4, may be achieved with so-called broadband lambda sensors (FIG. 1) in which additionally to the Nernst cell a second electrochemical cell, the so-called pump cell, is integrated. As described in the figurative part that follows, a voltage present at the pump cell is regulated such that a status of lambda=1 is constantly maintained in a cavity or measuring gap. The electric pump current induced in the process is proportional to the oxygen concentration, or, in values below zero, proportional to the O2-requirement in accordance with the inflowing fuel concentration, and therefore a measure for the value of lambda in the exhaust gas.

Furthermore, in the lambda=1 jump sensors described initially, it is known to maintain the sensor voltage at 450 mV in the start-up phase of the engine by means of a pilot control, via a voltage divider, for as long as the sensor is still too cold and no Nernst voltage corresponding to the oxygen concentration is present as sensor output signal. For in the cold state the sensor still has high internal resistance.

In contrast, the known broadband lambda sensors are operated using an evaluation circuit, which compares the Nernst voltage with an internally generated voltage of 450 mV. As soon as a deviation has occurred, it is increased in the circuit and injected into the pump cell as pump current. In this way, oxygen is pumped into or out of the cavity, and the Nernst voltage stabilizes at 450 mV. It is thus disadvantageous in these sensors that, during the start-up of the engine or the sensor, the Nernst voltage increases only slowly from 0V to 450 mV even if the exhaust gas is at lambda=1 the entire time. Because of this deviation, the amplifier applies the full positive pump voltage to the pump cell. Only after sufficient heating of the sensor will a high pump current set in that empties the cavity, despite the fact that the correct gas concentration lambda 32 1 had been present from the beginning. Thus, the output signal exhibits an overswinger in the lean direction, which seriously interferes with the regulation. Subsequently, the oxygen must be replenished again; in doing so, a small overswinger in the rich direction occurs again.

SUMMARY OF THE INVENTION

Consequently, the present invention is based on the objective of indicating a method of the type described in the introduction as well as a control device, which avoid a previously described disruption of the lambda control during the start-up phase of the engine or during the cold phase of the broadband sensor.

According to the present invention, the Nernst voltage is maintained at the nominal value of the reference voltage, such as 450 mV, with the aid of a pilot control, and it is kept there until the Nernst voltage is a measure of the oxygen concentration in the cavity of the pump cell of the broadband sensor. The pilot control is preferably realized by an ohmic resistor. In the process, a connection of a reference electrode in the control device is connected across the resistor to the reference voltage generated by an evaluation circuit, to which it is compared via a comparator of the circuit. The resistor is selected such that the Nernst voltage remains close to the nominal value of the reference voltage for as long as the Nernst voltage at lambda=1 has not yet reached the nominal value. In this context, a resistor in the range of 1 to 100 kOhm, preferably 10 kOhm, is used.

Accordingly, the present invention allows the operation of a broadband lambda sensor that has better starting performance than the related art. For one, it avoids all early pump currents that are caused only by the false Nernst signal. Nevertheless, true concentration deviations are rapidly corrected as a result of the high amplification in the evaluation circuit provided in these types of sensors. Furthermore, complicated suppressions of the sensor output signal or a switching-off of the pump voltage is avoided.

In contrast to the pilot control provided in lambda=1 jump sensors, the extreme reaction of the sensor caused by the mentioned high amplification is effectively avoided by high pump voltages. Furthermore, the influence of the pumped reference as "rich" pilot control is reduced.

In combination with a likewise pumped reference, the precontrol function and pumped reference function may be combined into one functional unit by selecting a voltage that is slightly above 450 mV. Since only the a.c. voltage portion is analyzed for the internal resistance measurement of the Nernst cell, there will be no control interference in this case either.

DETAILED DESCRIPTION

Figures 1, 2:
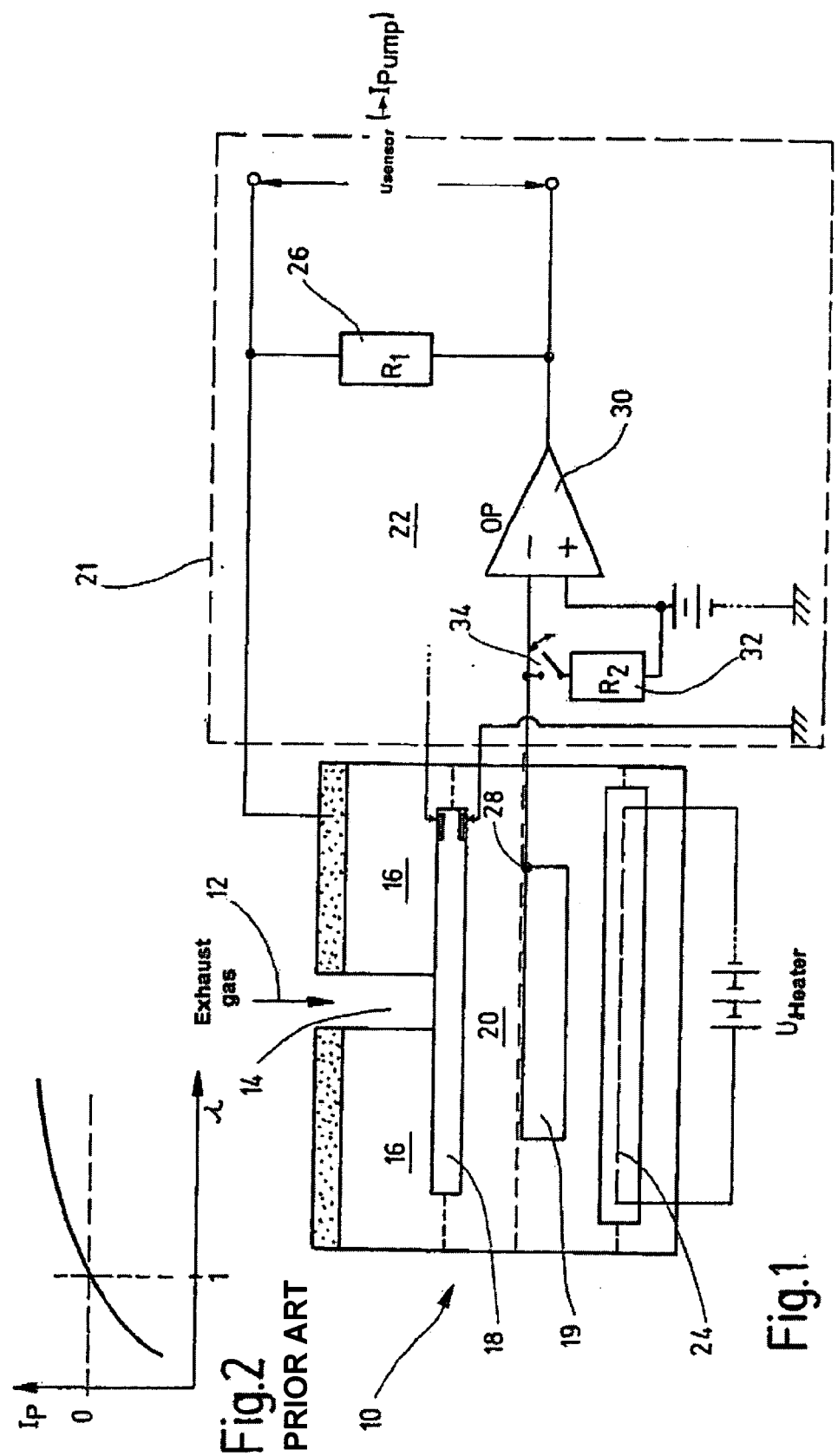
FIG. 1 shows a schematized, an exemplary embodiment of a broadband lambda sensor according to the present invention.
FIG. 2 shows a typical profile of pump current I_Pump as a function of lambda in a broadband lambda sensor.

In the broadband lambda sensor 10 shown in FIG. 1, exhaust gas 12 reaches the actual measuring chamber 18 of a Nernst cell 20 through a small orifice 14 in a pump cell 16, the so-called "diffusion gap", which acts as diffusion barrier. Adjacent to Nernst cell 20 is a reference gas chamber 19 containing an oxygen reference gas. Measuring chamber 18 is always set to a stoichiometric air-fuel ratio. An evaluation and control circuit 22 located in a control device 21 or similar device regulates a pump voltage U_Pump present at pump cell 16 in such a way that the composition of the gas in measuring chamber 18 remains constant at lambda=1. With lean exhaust gas 12, pump cell 16 pumps oxygen from measuring chamber 18 to the outside. On the other hand, when exhaust gas 12 is rich, the oxygen of exhaust gas 12 from the environment is pumped into measuring chamber 18, thereby reversing the direction of electric pump current I_Pump. The pump current is proportional to the oxygen concentration and/or oxygen requirement. In this way, pump current I_Pump is a measure for lambda in the exhaust gas. An integrated heater 24 maintains an operating temperature of at least 600 degrees Celsius, which, however, is reached only following a certain preheating period after a cold start.

Figure 6:
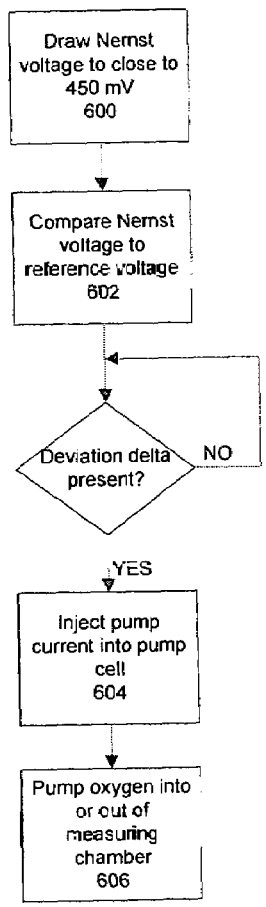
FIG. 6 is a flowchart that illustrates a procedure for operations of a broadband lambda sensor, according to an example embodiment of the present invention.

Referring to FIGS. 1 and 6, the pump current is set via evaluation and control circuit 22, which compares, at 602, Nernst voltage U_Nernst to an internally generated reference voltage U_Ref of 450 mV for determining the oxygen concentration of the exhaust gas. As soon as a deviation Delta (U_Nernst, U_Ref) is present, this deviation is amplified in circuit 22 and, at 604, injected as pump current I_Pump into pump cell 16. In this way, at 606, oxygen is pumped into or out of measuring chamber 18, and Nernst voltage U_Nernst stabilizes at 450 mV. The required pump current I_Pump or output voltage U_Sensor dropping via a resistor (R1) 26 is evaluated as output signal of sensor 10.

A 10 kOhm resistor (R2) 32 is interconnected in evaluation circuit 22, between a reference electrode 28 and the negative pole of operational amplifier (OA) 30 connected as comparator and the positive pole of OP 30. This ensures that, at 600, Nernst voltage U_Nernst is drawn to a value close to 450 mV for as long as the Nernst voltage at lambda =1 does not yet amount to 450 mV.

It must be noted that for the operation of a broadband sensor 10 having pumped reference the reference electrode is connected via a fixed resistor of 100 kOhm, for instance, to +5V, so as to provide a continuous supply of oxygen to reference gas chamber 19 via Nernst cell 20.

Output signal I_Pump is transmitted to an additional electronic control (not shown) which, via a control signal, in turn signals to a carburetion system, such as an injection system or an electronically controlled carburetor, whether the mixture must be enriched or made lean. If the mixture is too lean, more fuel is added; if the mixture is too rich, the fuel quantity conveyed to the engine is reduced again.

A typical qualitative profile of pump current I_Pump as a function of lambda is shown in FIG. 2. When the exhaust gas is lean, a positive pump current results so as to maintain a stoichiometric composition in the measuring chamber or the diffusion gap. On the other hand, in the case of rich exhaust gas a negative pump current is present. Since one is no longer dependent on the stepped voltage characteristic of the Nernst cell in this case, lambda is able to be measured continuously in a range of 0.7 to infinity. A measurement for lambda equal to infinity is required for overrun compensation, for example.

Figure 3A:
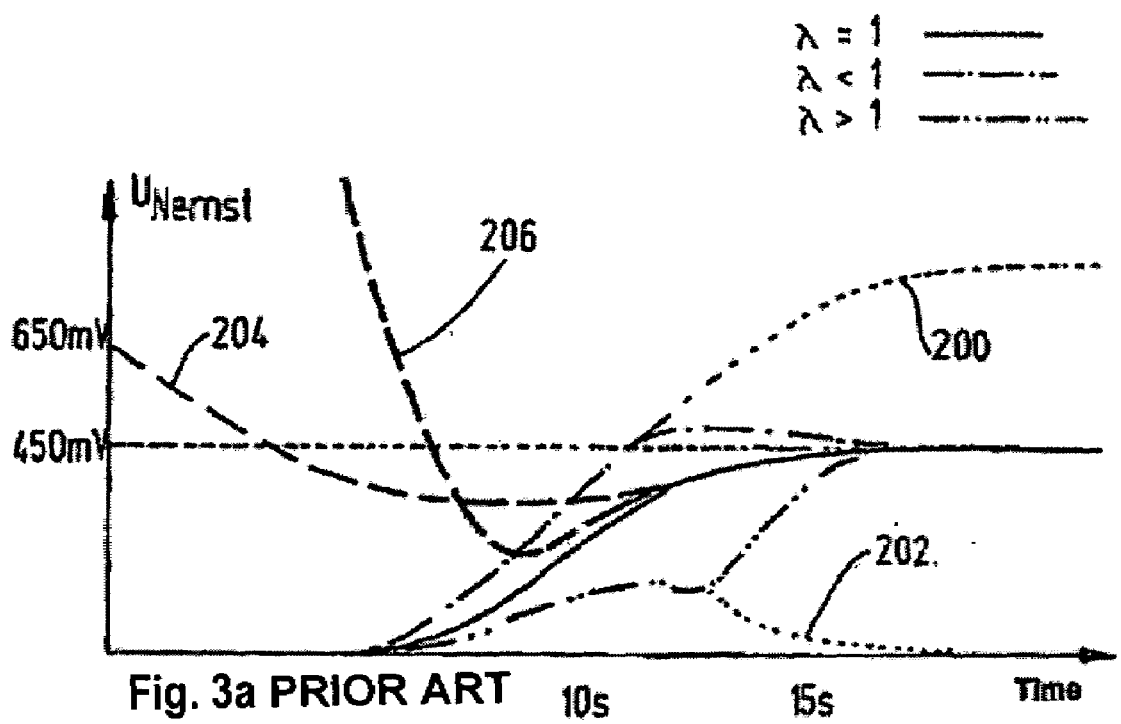
FIGS. 3a–c shows typical voltage profiles of Nernst voltage U_Nernst (a), pump voltage U_Pump (b), and of pump current I_Pump (c) according to the related art.
Figure 3B:
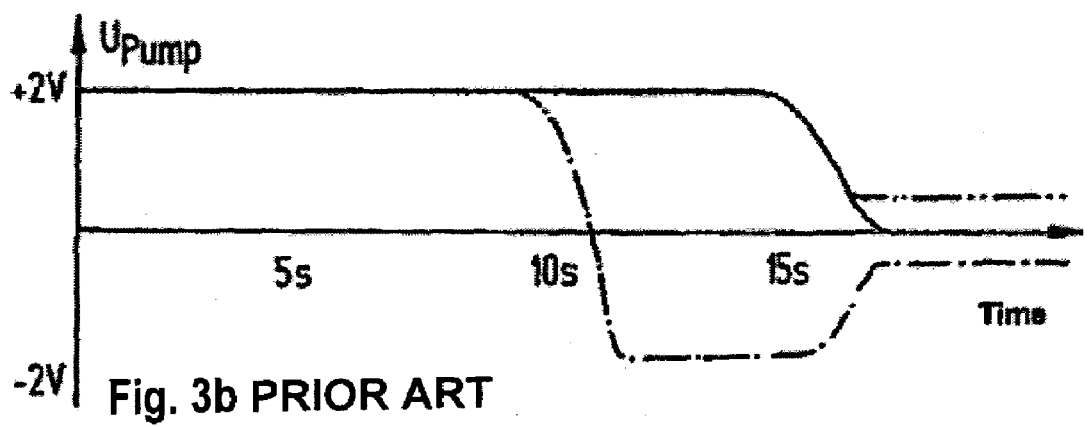
Figure 3C:
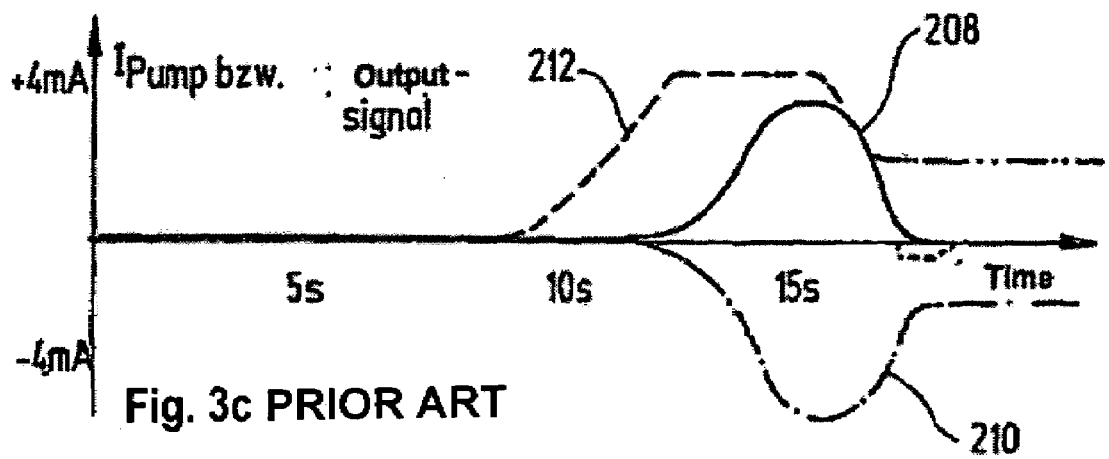

FIGS. 3a–c show voltage profiles of Nernst voltage U_Nernst as they typically occur in broadband sensors known from the related art, (a) without pilot control at lambda=1 shortly after starting the engine or the sensor, i.e., with a sensor that is still cold; as well as pump voltage U_Pump (b); and pump current I_Pump (c).

FIG. 3a illustrates voltage profiles for U_Nernst as they result in three qualitatively different lambda values, the solid line representing the Nernst voltage resulting with pumped reference at lambda=1 at which the signal begins with a positive battery voltage. The corresponding signal coming from U_Batt is denoted by 206. In the other measuring curves (represented by single or double dashed/dotted lines), the Nernst voltage initially starts from the value O V as well. In addition, in the temporally attenuating measuring curves, the profiles of the Nernst voltage resulting without regulation have been drawn in as dotted curves 200, 202 for comparison purposes.

As can also be gathered from FIG. 3a, the Nernst voltage increases only slowly from 0V to 450 mV when the sensor is started, notwithstanding the fact that the exhaust gas is at lambda=1 the entire time. Because of this deviation, the differential amplifier applies the full positive pump voltage U_Pump to the pump cell. As soon as the pump cell of the sensor has warmed up sufficiently, a higher pump current I_Pump also sets in due to U_Pump, which empties the cavity of oxygen. This procedure takes place although the correct gas concentration lambda=1 has been present already from the beginning.

Incidentally, profile 204 of U_Nernst, additionally drawn in as a dashed line in FIG. 3a, would result with a pumped reference coupled in in a low-ohmic manner according to the present invention, or with a resistance of 10 kOhm applied to 650 mV.

As can be seen in FIG. 3c, output signal U_Sensor, which is ascertained from I_Pump, shows an overswinger 208 in the "lean" direction, which interferes with the regulation. Subsequently, the oxygen must be replenished again; in the process, a small overswinger in the "rich" direction often occurs.

When operating with pumped reference, Nernst voltage U_Nernst is +5V for as long as the internal resistance of the Nernst cell is still very high. However, as soon as the internal resistance decreases, the Nernst voltage U_Nernst, which is still too low on account of the cold sensor, rises and pulls output signal U_Sensor below 450 mV. Here, too, output signal U_Sensor displays an overswinger 212 in the "lean" direction. Only when reference pump current I_Pump Ref of the pumped reference is selected very high will the sensor show an overswinger in the "rich" direction.

Furthermore, it must be differentiated between the start in the case of a compact design (cf. German patent application DE 199 41 051), the start in lean exhaust gas and the start in rich exhaust gas. In a start with a compact design, the pump cell is warmed up especially early. This increases the overswinger even more since the control deviation is converted into a pump current earlier. In a start in extremely lean exhaust gas, the overswinger already corresponds to the required pump current and thus has less of an effect as an error. However, here as well, too much oxygen is pumped out of the cavity in the process. Without pilot control, given a quickly heated pump cell, a lean overswinger still results in a start in rich exhaust gas. Only in a rich pilot control or in pumped operation does an overswinger of output signal U_Sensor occur in the rich direction.

Operating the pump cell at full pump voltage U_Pump places stress on the zirconium oxide used as ceramic body of the sensor, especially when there is a lack of oxygen in the cavity. In the extreme case, black discolorations may occur if the pump voltage is not limited. In particular in a continuous start in rich exhaust gas, a higher pump-voltage requirement results due to polarization of the electrodes.

Switching off pump voltage U_Pump with the aid of a control program within the first 15 seconds until the Nernst cell becomes operational, would be technically complex. Furthermore, an implementation would depend heavily on the application.

Figure 4A:
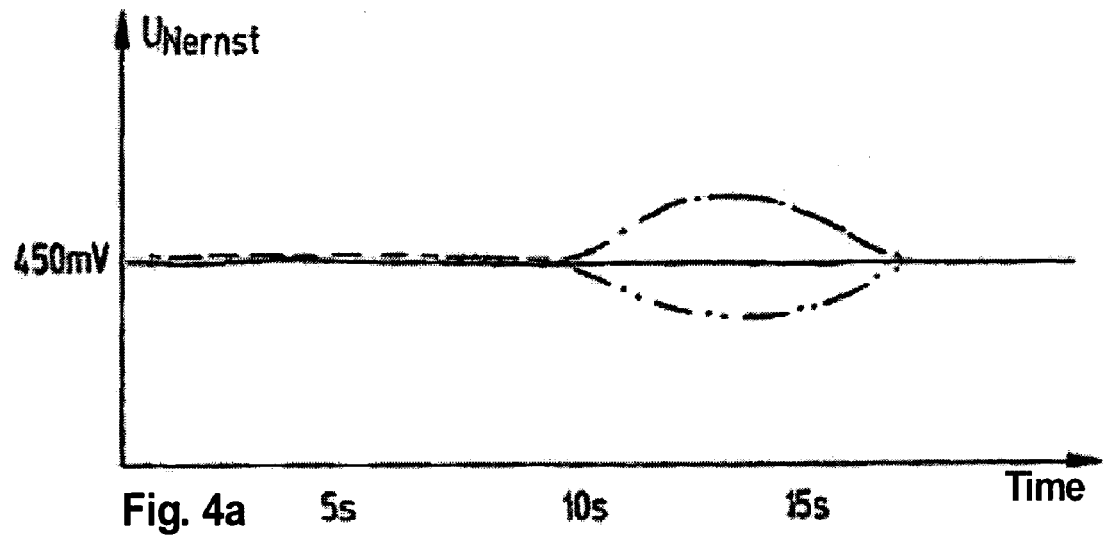
FIGS. 4a–c shows voltage and current profiles, comparable to FIGS. 3a –c, in a pilot control according to the present invention at lambda=1.
Figure 4B:
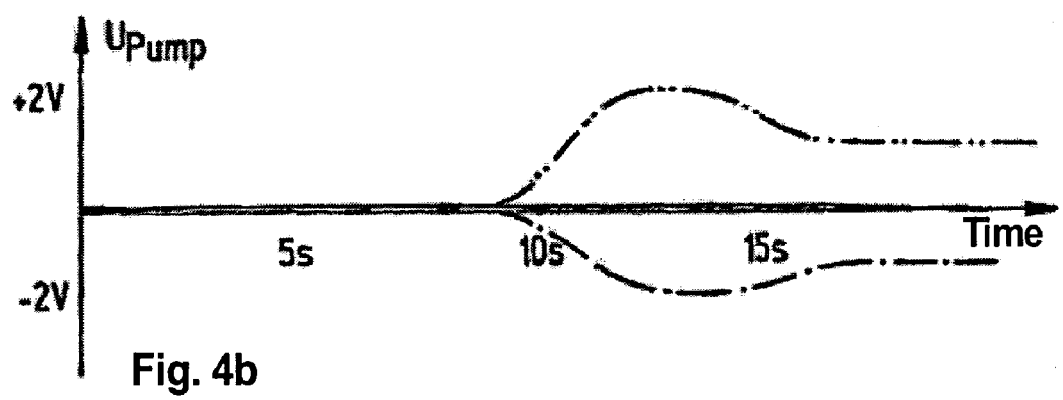
Figure 4C:
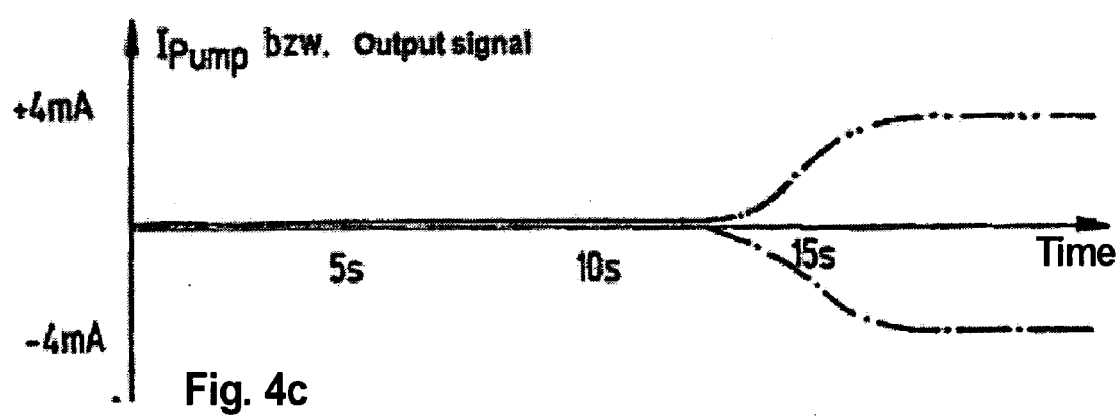

FIGS. 4a–c show voltage profiles that result at different measuring points of the circuit shown in FIG. 1, of Nernst voltage U_Nernst (FIG. 4a) and also of the pump voltage (FIG. 4b) and the pump current (FIG. 4c) given a pilot control according to the present invention at lambda=1. In these figures the resulting measuring curves of the mentioned variables are each compared in rich and lean starting operation of the engine.

According to the present invention, the Nernst voltage is maintained close to the nominal value of the reference voltage by means of the pilot control until the Nernst voltage is an actual measure of the oxygen concentration in the cavity of the pump cell. The criterion that the Nernst voltage is an actual measure for the oxygen concentration in the cavity of the pump cell is given by the fact that the resulting voltage corresponds to the voltage calculated according to the Nernst equation. This is detected, for example, via the internal resistance of the Nernst voltage source dropping below a predefined value of 300 Ohm, for instance.

The closer the Nernst voltage is to the nominal value of the reference voltage, the smaller the deviation of the Nernst voltage, for it is only then that an ion flow will occur leading to the equilibrium described by the Nernst equation. The smaller the deviation of the Nernst voltage applied via the pilot control from the nominal value of the reference voltage, the lower the deviations of the pump voltage and, consequently, of the output signal from its final value corresponding to the exhaust-gas composition. A limit value for the most recently named deviations results via the amplification factor of the pump-current controller.

The mentioned stabilization of the Nernst voltage is implemented in particular by means of an intervention in the input variable of the closed loop for the pump current. The advantages of such a procedure compared to the related art are their applicability to broadband lambda sensors, the reduction of the mentioned polarization of the pump electrodes as well as their effectiveness both in lean run-up and also in rich run-up of the catalytic converter during the start phase of the engine. In special applications the engine is operated in rich or lean operation during the run-up. This causes especially large deviations in the broad-band sensor (cf. FIG. 3c). It is these, in particular, that are avoided in the operating method according to the present invention (cf. FIG. 4c).

In the voltage curve shown in FIG. 4a, a pilot control of the sensor to 450 mV is achieved by the mentioned ohmic resistor. In the process, the connection of the reference electrode in the control device (FIG. 1) is connected, via a resistor of 1 to 100 kOhm, to reference voltage of 450 mV generated by the evaluation circuit or an evaluation IC, to which it is compared via a comparator of the circuit. The resistance is selected such that Nernst voltage U_Nernst remains close to 450 mV for as long as the Nernst voltage at LAMBDA=1 would not yet amount to 450 mV. A 10 kOhm resistor is preferably used. Because of the comparator, the Nernst voltage must not be exactly 450 mV. Given a lambda value that is not equal to 1, an amount-wise only slight overswinger or underswinger of the Nernst voltage results compared to the related art. At lambda=1, the overswingers or underswingers even disappear entirely.

As an alternative to the afore-described circuit, given a so-called "pumped reference", it is possible to select a resistance of 100 kOhm against a voltage of +2.5 V so as to inject a 20 μA pump current. As another alternative, given a pumped reference having low-ohmic in-coupling, it may be provided that the resistor for the pumped reference is connected to an only slightly higher voltage source, of 650 mV, for example. In the case of a pilot-control/pump resistance of 10 kOhm, a pump current of 20 μA results (cf. slashed line in FIG. 4a). The lower the ohmic resistance of the in-coupling to the voltage source, the smaller the deviation during warm-up of the engine, namely in accordance with the principles of the pilot control according to the present invention, which have been described in detail above.

Figure 5:
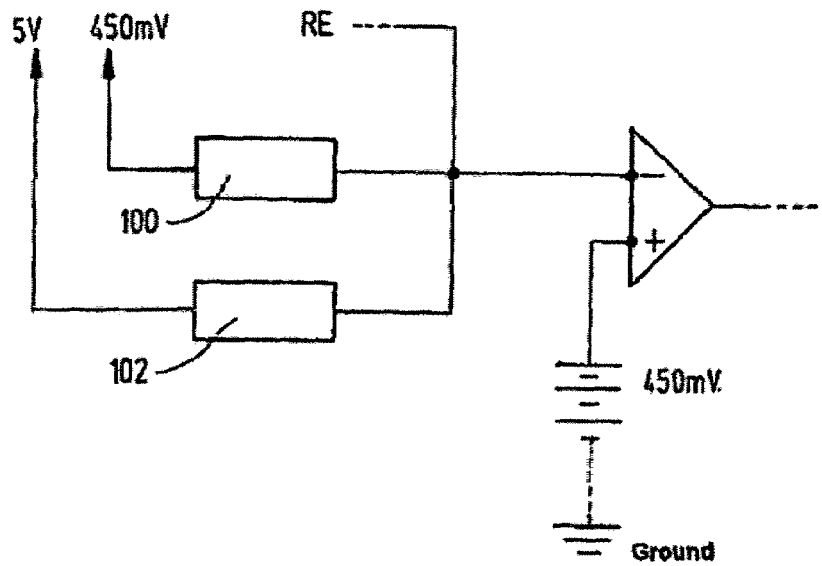
FIG. 5 shows a typical combination network to realize the pilot control according to the present invention.

The level of named voltage U results from the correlation U=R_in-coupling×20 μA+U_Nernst. Voltage U has the value 2.5 V relative to the virtual mass of the control circuit. Furthermore, any suitable combination networks are basically able to be used here as well. An exemplary embodiment of such a network is shown in FIG. 5. The resistor pair 100, 102 shown in FIG. 5 is able to be mathematically transformed to a specific resistance and a specific voltage.

Supplementing FIG. 4a, FIG. 4b shows the associated voltage profile of the pump current. The pumped reference is maintained in the known manner. Since no pump loading occurs in the time interval up to approximately 10 s, the mentioned polarization of the electrodes will not take place either.

FIG. 4c shows the pump current associated with FIG. 4a. The pump current represents the actual output signal of the regulation and, according to the present invention, has no overswingers, neither in rich nor in lean operation. The two curve profiles, beginning at approximately 15 s and tapering off in a flat manner, represent the measuring signal that results in each case in the warm operation of the sensor.

What is claimed is:

1. A method for operating a broadband lambda sensor, comprising:
   determining an oxygen concentration of an exhaust gas on the basis of a comparison of a Nernst voltage with a reference voltage having a nominal value;
   if a deviation is present between the Nernst voltage and the reference voltage, injecting a pump current into a cavity of a pump cell;
   regulating an electric voltage present at the pump cell such that lambda=1 holds in the cavity, the pump current being a measure for a value of lambda in the exhaust gas; and
   maintaining the Nernst voltage close to the nominal value of the reference voltage by way of a pilot control until the Nernst voltage is an actual measure for the oxygen concentration in the cavity of the pump cell.

2. The method as recited in claim 1, further comprising:
   implementing the pilot control by an ohmic resistor having an ohmic resistance; and
   connecting a reference electrode via the resistor to the reference voltage generated by an evaluation circuit.

3. The method as recited in claim 2, wherein:
   the ohmic resistance is between 1 and 100 kOhm.

4. The method as recited in claim 2, wherein:
   the ohmic resistance is 10 kOhm.

5. The method as recited in claim 1, further comprising:
   implementing the pilot control by way of a pumped reference; and
   selecting a 100 kOhm resistor against +5V so as to inject a 20 μA pump current.

6. The method as recited in claim 1, further comprising:
   combining the pilot control with a pumped reference; and
   connecting a resistor for the pumped reference to an only slightly higher voltage source of 650 mV for 20 μA pump current and 10 kOhm pilot control/pump resistance.

7. A control device for an operation of a broadband lambda sensor, comprising:
   an arrangement for determining an oxygen concentration of an exhaust gas on the basis of a comparison of a Nernst voltage with a reference voltage having a nominal value;
   an arrangement for, if a deviation is present between the Nernst voltage and the reference voltage, injecting a pump current into a cavity of a pump cell;
   an arrangement for regulating an electric voltage present at the pump cell such that lambda=1 holds in the cavity, the pump current being a measure for a value of lambda in the exhaust gas;
   an arrangement for maintaining the Nernst voltage close to the nominal value of the reference voltage by way of a pilot control until the Nernst voltage is an actual measure for the oxygen concentration in the cavity of the pump cell; and
   an ohmic resistor arranged between a connection of a reference electrode and a reference voltage of a comparator, the ohmic resistor maintaining the Nernst voltage close to the nominal value of the reference voltage for as long as the Nernst voltage does not yet amount to the nominal value at lambda=1.

8. The control device as recited in claim 7, wherein:
   an ohmic resistance of the ohmic resistor has a value in the range of 1 to 100 kOhm.

9. The control device as recited in claim 8, wherein:
   the ohmic resistance is 10 kOhm.

* * * * *